US008618178B2

(12) United States Patent
Roecken et al.

(10) Patent No.: US 8,618,178 B2
(45) Date of Patent: Dec. 31, 2013

(54) METHOD AND SUBSTANCES FOR TREATING T-CELL MEDIATED AUTOIMMUNE DISEASES

(75) Inventors: Martin Roecken, Tuebingen (DE); Kamran Ghoreschi, Oldenburg (DE); Christina Mathilde Weigert, Tuebingen (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 103 days.

(21) Appl. No.: 12/474,184

(22) Filed: May 28, 2009

(65) Prior Publication Data

US 2010/0004210 A1    Jan. 7, 2010

Related U.S. Application Data

(63) Continuation of application No. PCT/EP2007/009433, filed on Oct. 31, 2007.

(30) Foreign Application Priority Data

Nov. 29, 2006  (DE) .......................... 10 2006 058 183

(51) Int. Cl.
*A61K 31/13*       (2006.01)
*A61K 31/10*       (2006.01)
(52) U.S. Cl.
USPC ........................... 514/665; 514/667; 514/708
(58) Field of Classification Search
USPC ....................................... 514/665, 667, 708
See application file for complete search history.

(56) References Cited

U.S. PATENT DOCUMENTS

| 5,476,966 | A  | 12/1995 | Anderson et al. |
| 5,994,402 | A  | 11/1999 | Rotstein et al. |
| 2002/0164366 | A1 | 11/2002 | Sintov et al. |
| 2005/0079502 | A1 | 4/2005  | Hamuro et al. |
| 2005/0101646 | A1 | 5/2005  | Sang et al. |

FOREIGN PATENT DOCUMENTS

| EP | 1 354 601      | 10/2003 |
| WO | WO-00/48632    | 8/2000  |
| WO | WO-01/68069    | 9/2001  |
| WO | WO-02/100351   | 12/2002 |
| WO | WO-2004/003565 | 1/2004  |

OTHER PUBLICATIONS

Dringen et al., J. Neurosci. (1999) 19:562-569.
International Preliminary Report on Patentability for PCT/EP2007/009433, issued on Jul. 14, 2009, 15 pages.
International Search Report for PCT/EP2007/009433, mailed on Nov. 27, 2008, 6 pages.
Kibbe, ed., "Handbook of Pharmaceutical Excipients" $3^{rd}$ ed. (2000) American Pharmaceutical Association, pp. v-vii.
McIlwain et al., Oncogene (2006) 25:1639-1648.
Peterson et al., PNAS USA (1998) 95:3071-3076.
Schilling et al., Clinical and Experimental Immunology (2006) 145:101-107.
Suthanthiran et al., PNAS USA (1990) 87:3343-3347.
Utsugi et al., The Journal of Immunology (2003) 171:628-635.
Bekris et al., "Glutathione-S-Transferase M1 and T1 Polymorphisms and Associations with Type 1 Diabetes Age-at-Onset," Autoimmunity (2005) 38(8):567-575.
International Search Report for European Patent Application No. 11008821, dated Jul. 30, 2012, 7 pages.
Karg et al., "Modulation of Glutathione Level in Cultured Human Melanoma Cells," Acta Dermato-Venereologica (1989) 69(2):137-141.
Karg et al., "Alteration of Glutathione Level in Human Melanoma Cells: Effect of N-Acetyl-L-Cysteine and its Analogues," Pigment Cell Research (1990) 3:11-15.
Utsugi et al., "c-Jun N-Terminal Kinase Negatively Regulates Lipopolysaccharide-Induced IL-12 Production in Human Macrophages: Role of Mitogen-Activated Protein Kinase in Glutathione Redox Regulation of IL-12 Production," Journal of Immunology (2003) 171:628-635.
Communication for EP 11008821.8, mailed Oct. 8, 2013, 6 pages.

*Primary Examiner* — Renee Claytor
(74) *Attorney, Agent, or Firm* — Morrison & Foerster LLP (57) ABSTRACT

The invention relates to methods for treating T cell mediated autoimmune diseases, such as psoriasis and multiple sclerosis, in a human in need thereof, wherein a therapeutically effective amount of a substance which lowers the cellular glutathione content is administered to the human.

6 Claims, 10 Drawing Sheets

METHOD AND SUBSTANCES FOR TREATING T-CELL MEDIATED AUTOIMMUNE DISEASES

CROSS-REFERENCE TO RELATED APPLICATIONS

This application is a continuation of copending International Patent Application PCT/EP2007/009433 filed on Oct. 31, 2007, and designating the United States, which was not published under PCT Article 21(2) in English, and claims priority of German Patent Application DE 10 2006 058 183.0 filed on Nov. 29, 2006, which are incorporated herein by this reference in their entirety.

BACKGROUND OF THE INVENTION

1. Field of the Invention

The present invention relates to methods and substances for treating T-cell-mediated autoimmune diseases.

Autoimmunity is based on a specific, adaptive immune response against endogenous antigens. Normally, the immune system leaves endogenous substances undisturbed and combats only foreign bodies. Autoimmunity can be viewed as the result of a breakdown of the tolerance towards endogenous substances and/or of a defective control and regulation mechanism of the immune system. Admittedly the precise causes of the onset of autoimmune diseases are still unknown, however it is suspected that environmental and also hereditary factors are involved. T lymphocytes appear to be significantly involved in the triggering of the disease, since they can cause tissue damage both as cytotoxic T lymphocytes and also through the activation of macrophages.

Autoimmune diseases can be classified into tissue- or organ-specific and systemic, i.e., non-organ specific, autoimmune diseases. Thus for example the disease multiple sclerosis is an example of an organ-specific, T-cell-mediated autoimmune disease in man.

In practice, the therapeutic approach is limited by the chronic, slowly progressing nature of most auto-immune diseases. The use of immunosuppressants and corticosteroids has proved partially successful.

The course of chronic autoimmune diseases, allergies or infections can be predicted on the basis of the cytokine profile of CD4+ T helper ($T_H$) cells. The $T_H$ lymphocytes are further subdivided inter alia on the basis of the cytokines produced by them: while $T_H1$ cells synthesize interferon γ (IFN-γ) and interleukin-2 (IL-2), $T_H2$ cells instead produce interleukin-4 (IL-4), interleukin-5 (IL-5), interleukin-6 (IL-6), interleukin-9 (IL-9) and interleukin-13 (IL-13). A further $T_H$ cell population which produce cytokine IL-17, so-called $T_H17$ cells, have a similar inflammatory phenotype to $T_H1$ cells. IFN-γ producing $T_H1$ cells control intracellular pathogens, but, like $T_H17$ cells, can also trigger organ-specific autoimmune diseases such as for example autoimmune diabetes, multiple sclerosis or psoriasis, whereas IL-4 producing $T_H2$ cells can ameliorate organ-specific autoimmune diseases.

The differentiation of native CD4+ cells in either $T_H1$ or $T_H2$ cells is regulated by cytokines, in particular by IL-12 or IL-4, and also by T cell receptor-ligand interactions, accessory molecules and the like. In addition, the functional phenotype of dendritic cells (DC), which are either $T_H1$-inducing DC1 or $T_H2$-inducing DC2, plays a part. For the formation of $T_H17$ cells, the cytokine IL-23, which as well as its p19 chain has the same p40 subunit as IL-12, is necessary. Like IL-23, IL-12 is also produced by DC.

Glutathione (GSH) is a ubiquitously occurring tripeptide which is made up of the non-essential amino acids glutamate, cysteine and glycine. Because of its thiol group (SH group) and the γ-glutamyl linkage, glutathione has an abundance of biological functions which include detoxification reactions, structure formation of proteins, coenzyme functions, repair of DNA damage, and influencing of the cellular environment and hence involvement in developmental and ageing processes (ageing). Glutathione is possibly the most commonly occurring low molecular weight thiol and is found in almost all cells, in some cases at relatively high concentrations (about 5 mmol/l). The biosynthesis and degradation of glutathione proceed via the so-called γ-glutamyl cycle. As a sulfhydryl buffer in the cell, it is in equilibrium with glutathione disulfide GSSG, which is formed as an oxidation product either by catalytic action of a selenium-containing glutathione peroxidase, during which hydrogen peroxide arising in the metabolism is reduced, or in a transhydrogenation. An NADPH-dependent GSSG reductase catalyzes the reverse reaction to glutathione.

2. Related Prior Art

In recent studies (see Utsugi, et al., 2003, *J. Immunol.* 171, 628-635), it could be shown that compounds which are capable of forming glutathione-S conjugates inter alia suppress lipopolysaccharide-induced interleukin 12 production in macrophages.

In spite of said possibilities for treating autoimmune diseases, there is still great interest in finding alternative to the previously used therapeutic approaches, since said approaches often cause severe side-effects or can only be implemented very labor-intensively and/or at great expense.

SUMMARY OF THE INVENTION

The problem of the present invention is therefore to provide methods and substances for the prophylaxis and/or combating of autoimmune diseases.

According to the invention, this problem is solved through the provision of a substance lowering the cellular GSH level, where the substance is selected from the group comprising inhibitors of GSH synthesis, in particular L-buthionine sulfoximine (L-BSO) and GSH-depleting substances, in particular ifosfamid, diethyl maleate or acetaminophen. The problem is also solved by a method comprising the step of administering to a patient in need thereof, a therapeutically effective amount of a substance lowering the cellular GSH level, in particular of inhibitors of GSH synthesis, in particular L-buthionine sulfoximine (L-BSO) and GSH-depleting substances, in particular ifosfamid, diethyl maleate or acetaminophen.

The problem on which the invention is based is thereby completely solved.

From their own experiments, the inventors were able to show that through the lowering of the cellular GSH content in DC with representatives of said substances, the content of reactive oxygen species (ROS) rises and at the same time the production of IL-12 and IL-23 can be inhibited. As a result, development of the DC2 phenotype in the DC is triggered and the differentiation of IFN-γ producing $T_H1$ cells and IL-17 producing $T_H17$ cells thus suppressed, and instead the formation of IL-4 producing $T_H2$ cells is promoted. In contrast to the IFN-γ producing $T_H1$ cells or IL-17 producing $T_H17$ cells, these cannot trigger any organ-specific immune diseases.

In further experiments, the inventors have shown that through the use of for example L-BSO in experimental mice in which an experimental autoimmune encephalomyelitis (EAE) had been triggered, the course of the disease was markedly milder, and that some mice even remained healthy. In contrast to the control group, all the experimental animals to which L-BSO was administered survived.

Thus, through the present invention it was for the first time shown that through the controlled lowering of the cellular GSH level firstly the IL-12 and IL-23 production by DC, and as a result of this the IFN-γ and IL-17 production by T cells, can be lowered and thereby autoimmune diseases can be selectively and successfully treated.

In the present invention it is also shown that for treating autoimmune diseases, firstly inhibitors of GSH synthesis can be used, such as for example L-BSO, or else substances which produce GSH-S conjugates—and thus deplete GSH—and as a result lower the cellular GSH level and allow the cellular ROS level to rise.

Studies in patients with asthma have shown that certain GSH S-transferase genotypes are associated with the development of asthma, elevated IL-4 and IgE levels and decreased detoxification capacity. Thus a typical $T_H2$ disease of the lung is associated with a decreased detoxification capacity which is based on GSH.

Peterson, et al., (*Proc. Natl. Acad. Sci. USA*, 1998, 95:3071-3076) reported in said publication experiments in three immunological models in which a prolongation from the typical $T_H1$ cytokine profile to the $T_H2$ reaction schemes could be brought about through GSH depletion. However, this research group did not demonstrate any connection with autoimmune diseases.

The inventors were also able to show that GSH deprivation (due to targeted administration of substances which lower the GSH level), T cell cytokine production can also be influenced in man in vivo.

In the use according to the invention, it is particularly preferable if the autoimmune diseases are selected from the group comprising: multiple sclerosis, diabetes mellitus, rheumatoid arthritis, psoriasis, Crohn's disease, ulcerative colitis, celiac disease, systemic lupus erythematodes, eczematous diseases, transplant rejection, graft versus host reaction, and granulomatous diseases, in particular sarcoidosis and granuloma annulare. In contrast, typical $T_H2$-mediated diseases such as atopic asthma, allergic asthma and atopic or allergic rhinitis should improve through a glutathione-inducing approach with pharmaceutical substances such as N-acetyl-cysteine.

It is particularly preferable if the use is implemented in multiple sclerosis and psoriasis.

In multiple sclerosis, T lymphocytes, B lymphocytes and macrophages inter alia are to be found in the inflammatory foci (plaques), which is regarded as an indication of an autoimmune reaction. For treating multiple sclerosis, recombinantly produced interferon-β is in particular used at present, especially with the relapsing remitting disease course.

The autoimmune disease type 1 diabetes mellitus is due to cell-mediated chronic and irreversible destruction of the insulin-producing β cells of the pancreas, wherein a peptide present on the β cells is presumably recognized by autoimmune T lymphocytes, which in turn destroy the β cells.

Rheumatoid arthritis is an autoimmune disease, wherein through a modification of synovial cells an immune response by T lymphocytes, B lymphocytes and macrophages is induced, which leads to antibody formation against synovial cells. As a result, hydrolases, collagenases and lysosomal enzymes are released, which lead to the destruction of joint cartilage. Treatment is at present given with anti-inflammatory agents, corticosteroids and other antirheumatic drugs.

With the use according to the invention, an approach is demonstrated whereby a new alternative for treating the diseases enumerated is rendered possible. Indeed, the inventors were able to show in their own experiments that in mice with one administration of L-BSO inter alia, the course of an experimental auto-immune encephalomyelitis (EAE) could be markedly improved. The improved disease course—and the inventors could also demonstrate this—is directly linked to the lowering of the GSH levels, the rise in ROS and the differentiation of T cells into $T_H2$ cells associated therewith.

The invention further relates to a pharmaceutical composition which contains at least one of the claimed substances together with physiologically compatible additives and/or carrier substances.

Examples of such components are diluents, binders, suspension agents, lubricants, stabilizers and the like. These for example include, but are not limited thereto, water, salt solutions, alcohols, vegetable oils, polyethylene glycols, monoglycerides, etc. An overview of such components is for example to be found in A. Kibbe: "*Handbook of Pharmaceutical Excipients*", 3rd Edn. 2000, American Pharmaceutical Association and Pharmaceutical Press.

The composition is appropriately formulated, depending on the administration of the pharmaceutical composition, i.e., oral, parenteral, buccal, nasal, transdermal or intradermal, i.e., for example in the form of capsules, depot capsules, tablets, as liquid preparations which are injected, or else as formulations which are administered via pumps. Thus administration can also be effected subcutaneously or intravenously. Further, depending on the patient and the disease, the administration can be effected systemically or locally and subtly targeted. Furthermore, a combination of two or more substances which lower the GSH level can be used in the pharmaceutical composition.

Further, it is preferable if the use is implemented at a dose of ca. 0.001 mg/kg body weight of a patient to ca. 100 mg/kg body weight of a patient.

The invention further relates to a method for determining the potential of pharmaceutical substances to lower the glutathione content of cells, comprising the following steps:

a) incubation of cells with different concentrations of the given pharmaceutical substance to be tested; and, subsequently, b) determination of the glutathione content of the cells in comparison to control cells.

Here it is preferable if the method is implemented in vitro or ex-vivo.

Here, "in vitro" implementation of the method according to the invention for testing the potential of pharmaceutical substances to lower the glutathione content of cells means that cells, for example antigen-presenting cells or dendritic cells, are incubated in vitro with different concentrations of the given pharmaceutical substance to be tested. After a certain incubation time, preferably after 1 hour, 2 hours, 24 hours or 48 hours, the glutathione content of the cells is then determined in comparison to control cells.

For the determination of the glutathione content, after the incubation time, the cells are lysed and incubated on ice. The lysate is then high-speed centrifuged and the supernatant used for the GSH measurement, and the sediment prepared for the protein assay (for example after Lowry). Here it is preferable if the cells are lysed with sulfosalicylic acid (SSA), preferably by 1% sulfosalicylic acid.

The samples thus prepared and a GSH standard are next diluted in a microtiter plate and the assay reaction started by addition of a reaction mix which contains glutathione reductase. Next, the rise in the extinction at 405 nm is measured at 30 sec intervals for 10 mins with a microtiter plate reader, and the glutathione content determined using a calibration curve.

Here, when the glutathione disulfide (GSSG) content of the cells, i.e., the oxidized form of glutathione is measured, it is preferable that the GSH, i.e., the reduced form in the sample, is masked for example with 2-vinyl-pyridine at a pH between 5 and 7.

For the measurement of the protein content of each sample, the cell pellet is dried after the lysis. The determination of the protein content can preferably be effected by the method of Lowry (see for example Dringen, et al., "Supply by Astrocytes of CysGly as Precursor for Neuronal Glutathione", *J. Neurosci.* 1999, 19:562-569).

For the implementation of the method according to the invention ex vivo, the pharmaceutical substances to be tested are administered to the desired individuals (mammals). Then, after the treatment, small tissue pieces are removed from the relevant organs and the cells contained in these tissues/organs are prepared and appropriately tested, i.e., the further GSH and protein determination is effected in accordance with the procedure described for the in vitro method.

In a final step, comparison with the GSH content of control cells or control tissue in each case indicates the GSH-lowering action of the pharmaceutical substance to be tested.

The invention relates to a method for determining the potential of pharmaceutical substances, to increase the ROS content of cells, comprising the following steps:

a) incubation of cells with different concentrations of the given pharmaceutical substance to be tested; and, subsequently, b) staining of the cells with at least one chemiluminescent or fluorescent substance for determining the potential to induce ROS.

With the method according to the invention, reactive oxygen species (ROS) are measured. For this, the fluorescent dye 2',7' dichlorofluorescein diacetate ($H_2$ DCFDA) is preferably used. The absorption spectrum of this substance is 492-495 nm and the emission spectrum lies in the range between 517-527 nm. On induction of cell stress, e.g., by the administration of reagents giving rise to ROS, oxidation of the $H_2$ DCFDA to DCFDA+$H_2$ takes place. The fluorescence arising during this can be detected by flow cytometry (FL1).

Alternatively, for example a lucigenin-intensified chemiluminescence or a coelenterazine-intensified chemiluminescence can be used. For fluorimetric assays, apart from 2',7' dichlorofluorescein diacetate ($H_2$ DCFDA), dihydroethidium is also suitable. Further, photometric methods can be used by many of which, for example, cytochrome C reduction or NBT reduction is detected. Alternatively, electron spin resonance and spin trapping can also be mentioned as suitable detection methods.

The methods according to the invention are also described as "drug screening" methods, and offer the possibility of deliberately selecting substances with regard to their ability to lower the glutathione content of cells, or to raise the ROS content. The substances "positively" screened in this sense can then be used in the context of a therapy for the diseases enumerated further above. Thus the method according to the invention represents a method for the identification of new medicaments which can either serve for the therapy of the diseases mentioned further above, or for the identification of medicaments with antiallergic/antisclerotic action, with which $T_H2$ diseases such as allergic/atopic asthma and allergic/atopic rhinitis or IgE-mediated diseases (allergies) or fibrosing/sclerosing diseases (scleroderma, pulmonary fibrosis, hepatic fibrosis) can be treated with GSH-inducing, ROS-lowering pharmaceutical substances such as N-acetylcysteine.

The invention further relates to a method for determining the genetic susceptibility to developing an autoimmune disease, comprising the following steps:

a) obtention of peripheral blood leukocytes; subsequently b) isolation of the genomic DNA from the peripheral blood leukocytes; and, subsequently c) determination of the genotypes of the glutathione S-transferases (GST) using real time PCR and/or gene chips.

This method offers the advantage that the tendency of individuals to develop an autoimmune disease can be determined in a simple manner via the determination of the glutathione S-transferases.

For this, in the method according to the invention peripheral blood leukocytes are obtained and genomic DNA isolated therefrom. Using, e.g., real-time PCR, the genotypes of the glutathione S-transferases (GST) can be determined. As a result polymorphisms can be elucidated. The corresponding primer sequences for the GST families are known (see for example McIlwain, et al., "Glutathione S-transferase polymorphisms: cancer incidence and therapy", *Oncogene* (2006) 25:1639-1648).

The metabolism and the detoxification of reactive oxygen intermediates (ROI) is to some extent dependent on the members of the GST family, in particular GSTM1, GSTT1 and GSTP1. Theoretically, people who are homozygotic for GSTM1 or GSTT1 null genes can eliminate ROI more slowly and are thus exposed to a higher risk of intracellular cell damage due to ROS. Recent studies have shown that GSTM1 and GSTP1 have adjuvant effects in the onset of allergic asthma. The PCR-based determination of the GST genotypes can therefore detect a genetic susceptibility for the development of autoimmune diseases and at the same time also give pointers for the meaningful use of glutathione-depleting substances.

Apart from the PCR, a further screening method can also be used, for example the Affymetrix GeneChip® technology. Through the introduction of human exon array technology, it is now also possible to perform high-resolution analyses which also take account of the splicing of genes or exon clusters. Such high-resolution gene arrays make it possible to detect the genes for the GST in patients precisely and thus indicatively to determine susceptibility for autoimmune diseases or therapy with glutathione-depleting substances.

This genetic screening of patients as regards their GST genotypes and the functional analysis of the GSH/GGSG modulation serves for the pretreatment determination of the susceptibility for a therapeutic response to GSH-depleting pharmaceutical sub-stances. This is of particular interest and importance since in man, owing to different genotypes of the glutathione S-transferases, there is varying ability to eliminate ROS and to replenish the cellular glutathione content. Thus the possible therapeutic response can be graded in advance before introduction of a therapy with said substances.

Further advantages follow from the figures and the following example.

It goes without saying that the features mentioned above and those still to be explained below are usable not only in the combination stated in each case, but also in other combinations or alone, without departing from the scope of the present invention.

The present invention will now be explained in more detail on the basis of embodiments of the application, which are purely illustrative and do not in any way limit the scope of the invention. Reference is made to the appended drawings, which show:

DETAILED DESCRIPTION OF PREFERRED EMBODIMENTS

Example I

1. Material and Methods 1.1 Experimental Animals

Female SJL mice, C57BL/6, OVA transgenic DO11.10-BALB/c mice and BALB/c mice were either bred or bought (Charles River Laboratories, Harlan) and kept under specific pathogen-free conditions. The animal experiments were officially approved.

1.2

For the measurement of reactive oxygen species (ROS) in DC and APC, the fluorescent dye 2',7' dichlorofluorescein ($H_2$ DCFDA, Molecular Probes, Eugene, USA) was used. $5 \times 10^5$ DC were preincubated in 1 ml of RPMI medium (without mercaptoethanol) for 60 mins at 37° C. in the incubator with 1% DMSO or 10 µg/ml DMF+/−NAC (1 mM) or GSX (1 mM). After this preincubation, 1 µM/ml $H_2$ DCFDA was added and the cells incubated for a further 30 mins at 37° C. Within one hour, the fluorescence produced was detected using flow cytometry (FL1).

1.3 Glutathione Determination

Cellular GSH and GSSG were determined in micro-titer plate assays using colorimetric methods. The cellular GHS content is determined as a percentage of the GSH levels in freshly prepared controls or as pmol $10^{-6}$ cells. GSSG was not detectable.

1.4 Cytokine Assays

IL-4, IL-10, IL-12 and interferon-γ were determined using the ELISA (enzyme linked immunosorbent assay) set or with the use of individual components from BD BioSciences. IL-23 in the supernatant was determined using the ELISA set (eBioscience). For intracytoplasmic cytokine analyses, the T cells were restimulated with PMA/ionomycin or with APC and peptide in the presence of brefeldin A, then fixed and permeabilized and stained. For the surface staining, anti-CD4 or KJ1-26 antibodies were used; the cytokine antibodies (PE labeled) were all obtained from BD Pharmingen.

1.5 Antigen Presenting Cells

As antigen presenting cells (APC), T cell depleted spleen cells from syngenic mice were used. Dendritic cells (DC) which were obtained from bone marrow (BMDC) and cultured with GM-CSF were used for the relevant experiments on day 7 of culturing. For the experiment, in each case an equal number of APC were cultured either with the medium alone, with L-BSO ($C_8H_{18}N_2O_3S$, 0.5 mM), dimethyl sulfoxide DMSO($C_2H_6OS$), dimethyl fumarate DMF ($C_6H_8O_4$, dissolved in DMSO, 70 µM), or calcium monomethyl fumarate (MMF; $CaC_{10}H_{10}O_8$, 200 µM). All substances except for MMF (Fumapharm) were purchased from Sigma-Aldrich. At the respective stated times (see below) the cells were either analyzed directly for their GSH content, used for T cell stimulation or stimulated for IL-2 production with *Escherichia coli* lipopolysaccharides 055.B5 (Sigma-Aldrich) or CpG-DNA 1668 (MWG Biotech) and IL-4 (Stratmann). In order to raise the GSH level again, 1 mM GSH-OEt ($C_{12}H_{21}N_3O_6S$; Sigma-Aldrich) or 1 mM NAC (Sigma-Aldrich) was added. The GSH reservoirs in mice were depleted by feeding with DMF or MMF, and in man by treatment with Fumaderm®.

1.6 T Cells and T Cell Stimulation

The CD4+ T cells of DO11.10 mice were sorted using MACS magnet beads (Miltenyi Biotech). By culturing of DC on day seven with either medium and DMSO or DMF for 2 hours, $DC^{GSHhigh}$ or $DC^{GSHlow}$ could be generated. After four-hour stimulation with LPS or CpG-DNA/IL-4, the $DC^G_{SHhigh}$ or $DC^{GSHlow}$ were used for the stimulation of DO11.10 T cells with 10 µg/ml ovalbumin peptide 323-339 for two days. The T cells were expanded with 50 U/ml IL-2 (Chiron Therapeutics). The cells were washed on day 10 and restimulated with fresh APC. The analysis was performed with the supernatants after 24 hrs. CD4⁺ T cells were obtained from SJL mice immunized with PLP peptide using MACS magnet beads and stimulated with irradiated APC and PLP peptide 139-151 in the presence of L-BSO, DMF or only in medium as control.

1.7 PLP-specific T Cells and EAE

Spleen and lymph node CD4⁺ T cells were stimulated with PLP (proteolipid protein) peptide 139-151 (10 µg/ml) and stimulated for four days with irradiated SJL-APC in the presence or absence of L-BSO (0.5 mM, Sigma), expanded for three to four days and then restimulated for cytokine production (proteolipid protein is the commonest myelin protein in the central nervous system and plays an important part as an autoantigen in the onset of multiple sclerosis). Next, $10^7$ sham (control) or L-BSO treated T cells were injected intraperitoneally into naive SJL mice and the EAE developing as a result was observed. For treating actively induced EAE, SJL mice were immunized with 75 ng in 4 mg/ml complete Freund's adjuvant (CFA), then 200 µg of pertussis toxin were injected intraperitoneally and the mice were observed with regard to the development of EAE. Half of the group was fed daily for 14 days with DMF 0.3 mg/ml (Fluka) or L-BSO 0.15 mg/ml in the drinking water. For the cytokine analysis of PLP-specific T cells, the draining lymph nodes of the SJL mice were removed 6 days after the immunization and CD4⁺ T cells antigen-specifically analyzed (ELISPOT). For this, ELISPOT plates (Millipore Corporation) were coated with anti-IFN-γ or anti-IL-4 antibodies overnight at 4° C., blocked after 12 hrs with PBS/10% FCS and, after the solution had been poured off, the isolated T lymphocytes were incubated with APC and medium alone or in the presence of PLP peptide. After the incubation time, the cells were poured off, and the plates washed with PBS/Tween and incubated with biotin-conjugated secondary antibodies. After further washing procedures and incubation with streptavidin-alkaline phosphatase (Boehringer), the plates were incubated with developer solution. After washing with $H_2O$, the number of spots was determined in the ELISPOT reader (Biosys).

1.8

DC from human bone marrow (BMDC) (CD14⁺) were isolated using MACS (Miltenyi Biotech) and incubated for seven days with IL-4 (500 U/ml, R & D Systems) and GM-CSF (Granulocyte-Monocyte Colony Stimulating Factor) (1000 U/ml (Immunonex)). GSX determination as under 1.3.

1.9 Psoriasis Therapy and Clinical Evaluation

Patients with severe psoriasis were treated with Fumaderm® (Hermal). The severity of the patients' disease was determined using the "Psoriasis Area and Severity Index" (PASI).

1.10 Ex vivo Cytokine Analysis of Human T Cells

The ex vivo cytokine pattern of the T cells was determined at the stated times (see below), this being each time that the routine blood analysis was performed on the Fumaderm® patients. PBMC were isolated from heparinized blood by ficoll gradient centrifugation and directly stimulated for four hours with phorbol myristate acetate (PMA); 5 ng/ml) and ionomycin (0.5 µg/ml) in the presence of brefeldin A (3 µg/ml) (each from Sigma). Next, surface staining was performed with fluorescein thiocyanate (FITC)-conjugated monoclonal antibodies—either against CD4 or CD8—and intracellular staining with phycoerythrin (PE)-conjugated monoclonal antibodies against IL-4 or IFN-γ (BD Pharmingen) according to the manufacturer's protocol. Further, isotype controls were performed to ascertain the gates. The samples were analyzed with an FACScan™ (BD Biosciences). For the in vitro studies of the T cells, PBMC were stimulated for three days with 100 ng/ml staphylococcal enterotoxin B (SEB) in the presence or absence of DMF (Sigma-Aldrich), and the cells were then expanded with IL-2. On day 13, the cells were stimulated with PMA and ionomycin and the intracellular IL-4 or interferon-γ content was determined by FAGS analysis.

2. Results

Figure 1A:
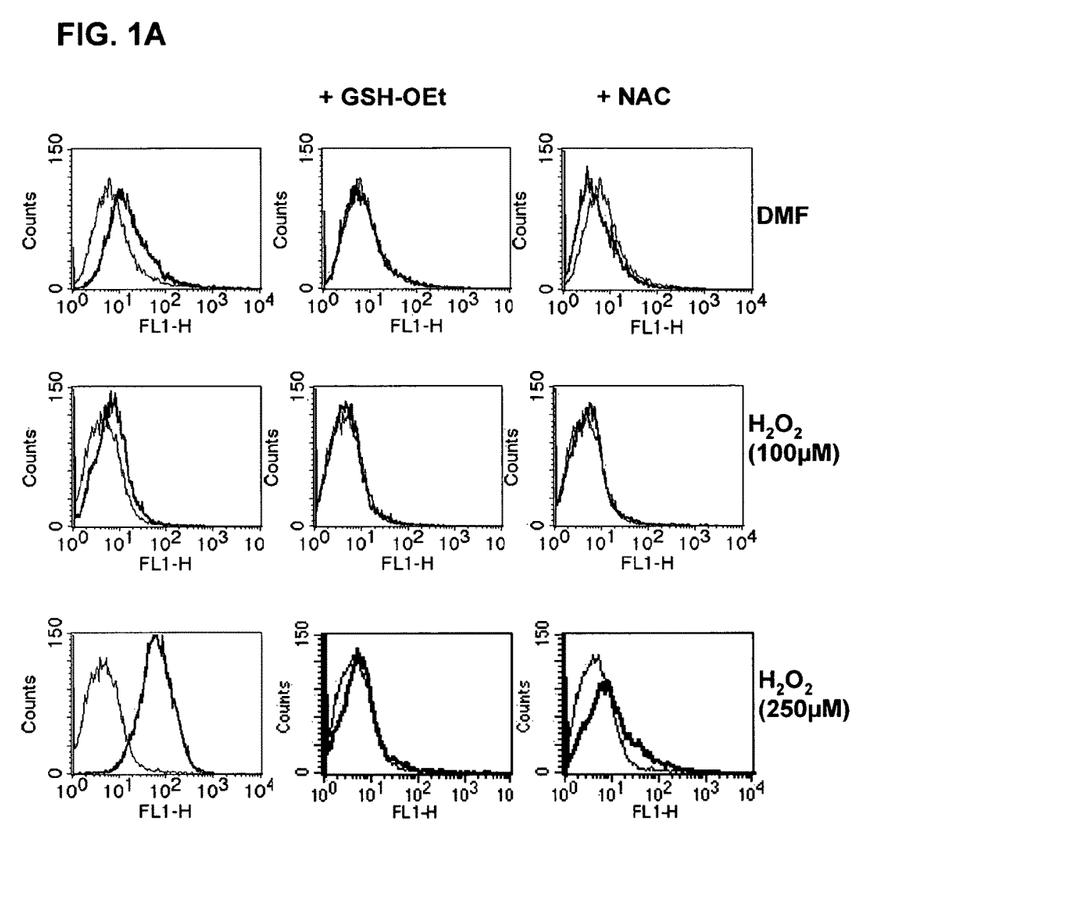
FIG. 1A. Flow cytometry analyses (dichlorofluorescein): induction of ROS in BMDC by glutathione depletion with DMF or $H_2O_2$ (100 µM or 250 µM), and the rise in ROS production due to exogenous administration of glutathione GSH-OEt or the glutathione inducer N-acetylcysteine (NAC).
Figure 1B:
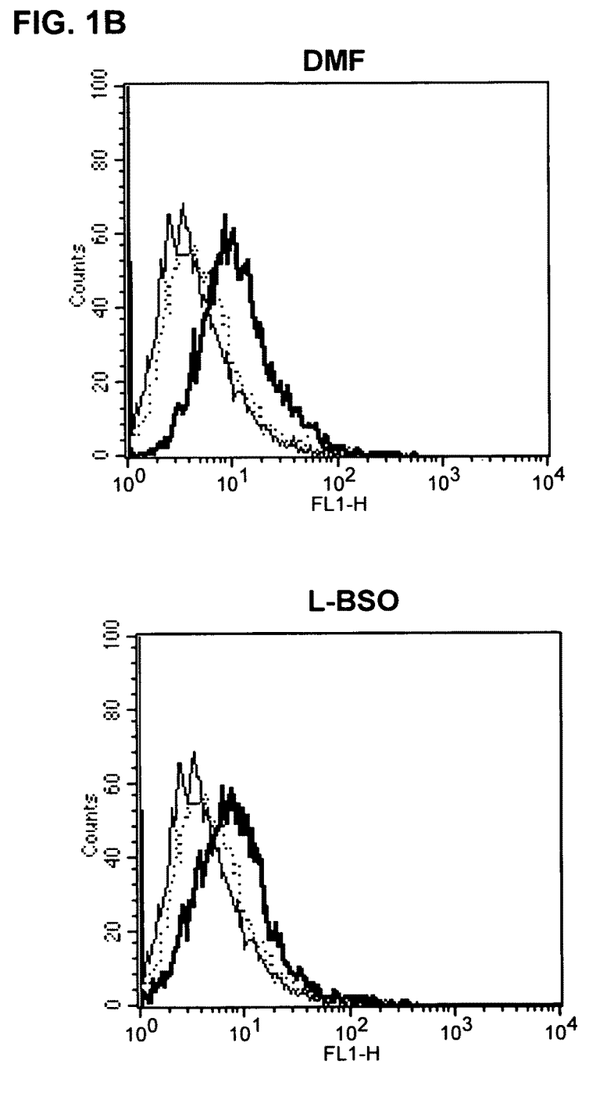
FIG. 1B. Flow cytometry analyses (dichlorofluorescein): the induction of ROS in BMDC by DMF or L-BSO.
Figure 1C:
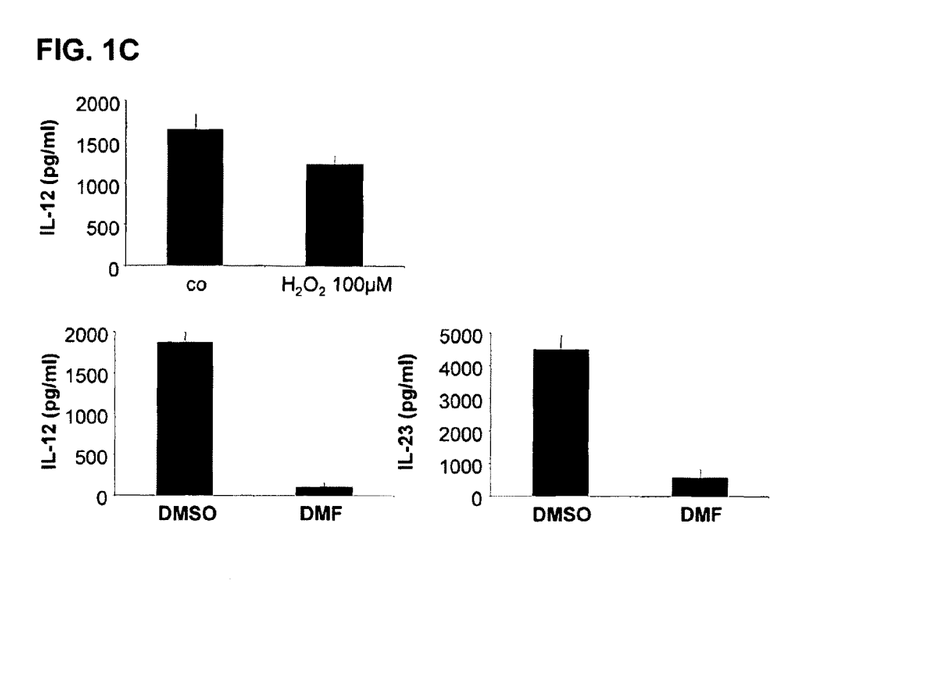
FIG. 1C. Determination of IL-12 and IL-23 in culture supernatants using ELISA: ROS such as $H_2O_2$ lower the production of IL-12. DC treated with DMF produce markedly less IL-12 and IL-23 compared to controls (DMSO) after stimulation with LPS.
Figure 1D:
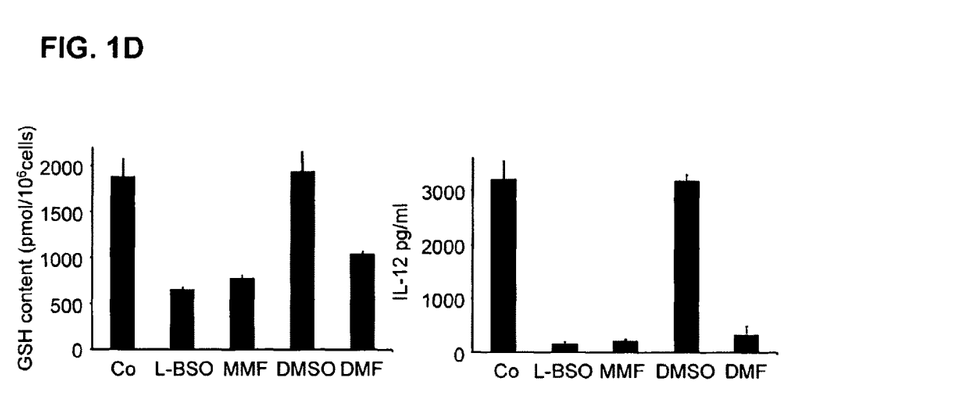
FIG. 1D. Colorimetric determination of GSH content and ELISA determination of IL-12 content: DMF, but also MMF and L-BSO, lead to a marked decrease in the intra-cellular GSH content and associated with this to a markedly decreased capacity to produce IL-12.

Glutathione is a central intracellular molecule which is involved in many metabolic processes such as the detoxification of intracellular oxygen radicals (reactive oxygen species, ROS). Oxidative stress with hydrogen peroxide ($H_2O_2$) from DC can be made visible with dichlorofluorescein (DCF) (FIG. 1A). Glutathione depletion due to L-BSO leads to a rise in intracellular ROS in DC (FIG. 1B). Likewise, the glutathione S-conjugate forming agent DMF can lead to a rise in ROS in DC (FIG. 1A+B). This DMF-induced ROS increase can be completely neutralized by addition of GSH ethyl ester (GSH-OEt) or NAC (FIG. 1A). The addition of DMF, MMF or L-BSO induces ROS in DC and at the same time depletes the intracellular glutathione level of DC (FIG. 1D). These DC exhibit strong suppression of IL-12 production (FIG. 1C+D). Apart from IL-12, the production of IL-23 is also determined by the intracellular glutathione content (FIG. 1C). Glutathione depletion in DC with DMF lowers the LPS-induced IL-23 production in DC cultivated from bone marrow up to 10,000-fold (FIG. 1C). At the same time, DMF induces a rise in IL-10 production in DC.

In order to exclude the possibility that the individual compounds have some kind of pharmacological effect on IL-12 synthesis, the intracellular GSH loss was prevented by addition of exogenous GSH-OEt. The inhibition of the intracellular GSH deprivation in turn neutralized the IL-12 suppression (FIG. 2A), which demonstrates that the DC need a $GSH^{high}$ status in order to produce IL-12. The addition of NAC showed the same effects as GSH-OEt (not shown).

Figure 2A:
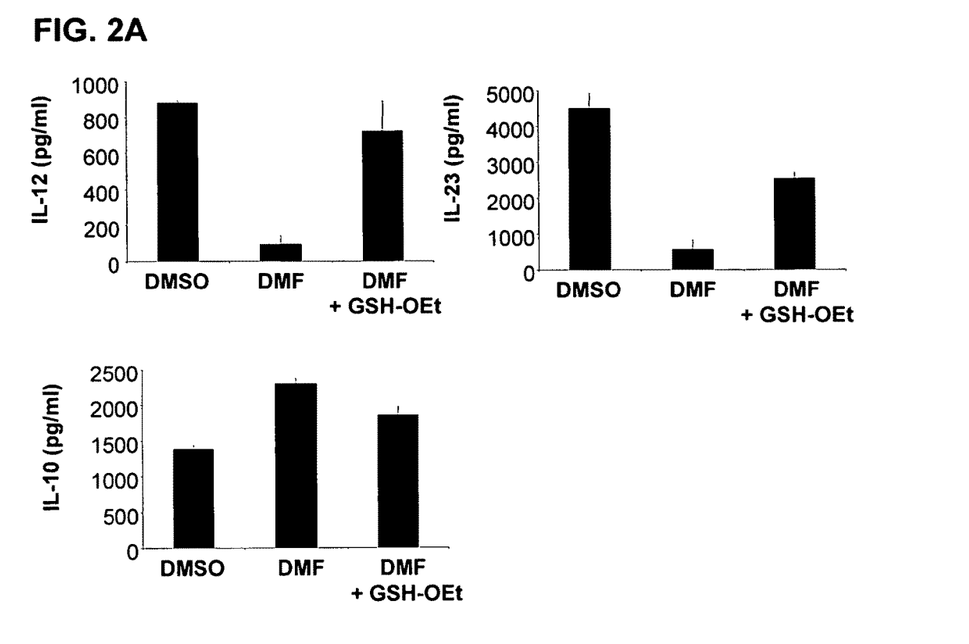
FIG. 2A. Determination of IL-10, IL-12 and IL-23 in culture supernatants using ELISA: the intracellular GSH content deter-mines the phenotype of the DC. $DC^{GSHhigh}$ produce IL-12 and IL-23 and exhibit a DC1 phenotype, whereas $DC2^{GSHlow}$ do produce IL-10, but hardly any IL-12 and IL-23. The glutathione-depleting and DC2-inducing effect of DMF can be completely neutralized by the simultaneous exogenous administration of GSH. The DC again replenished with GSH exhibit a DC1 phenotype.

Furthermore, the addition of GSH-OEt to DMF again restored IL-23 production in DC and decreased IL-10 production in DC (FIG. 2A). These results show that the GSH content determines the DC phenotype and cytokine production.

Figure 2B:
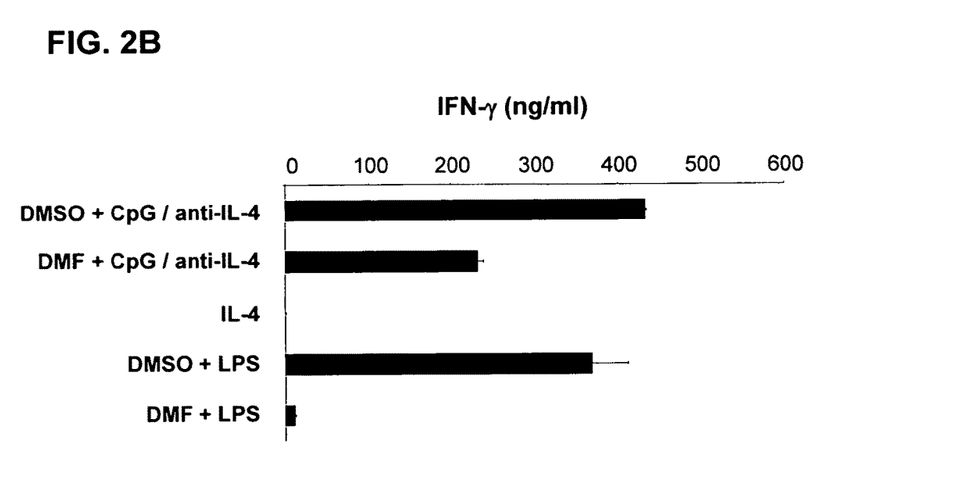
FIG. 2B/C. Determination of IFN-γ and IL-4 using ELISA: the intracellular GSH levels determine the functional phenotype IL-12$^+$DC1$^{GSHhigh}$ or IL-12$^-$DC2$^{GSHlow}$ and thus the differentiation of TCR-transgenic T cells towards IFN-γ producing Th1 cells or IL-4 producing Th2 cells.
Figure 2C:
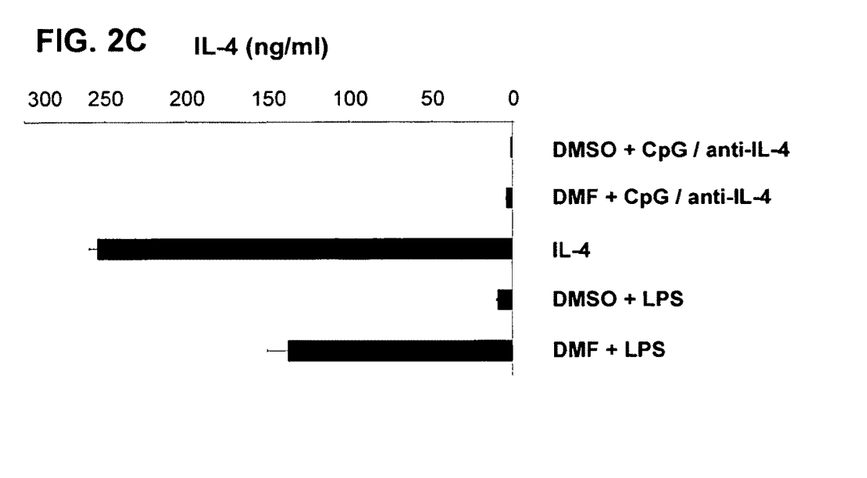
Figure 2D:
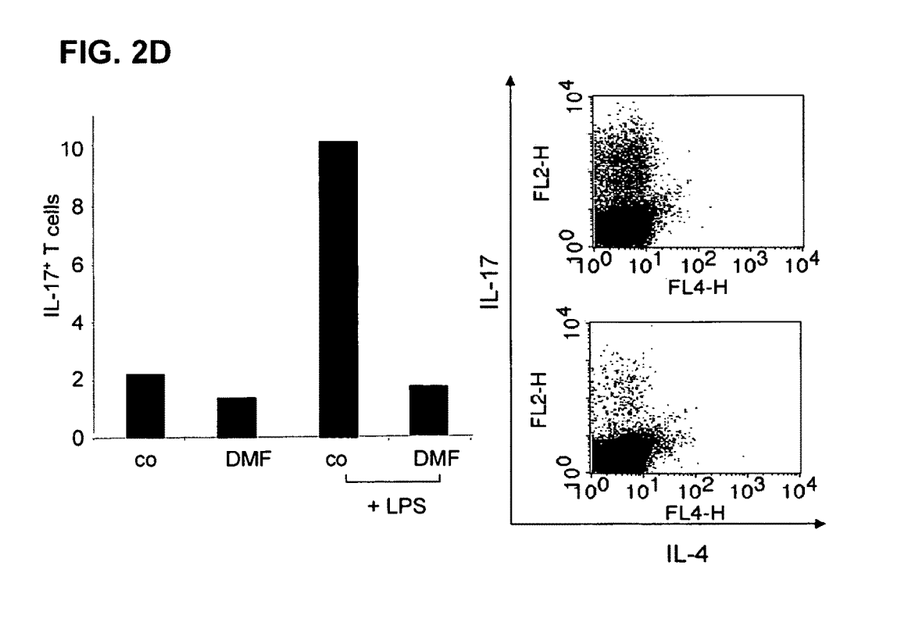
FIG. 2D. Determination of IL-17 using ELISA: in the same way, the intracellular GSH levels determine the functional phenotype of IL-23$^+$DC$^{GSHhigh}$ or IL-23$^-$DC2$^{GSHlow}$ and thus the generation of Th-17$^+$ cells or Th-17$^-$ cells. The FACS diagrams on the right show the control above, and DMF below.

In order to show that the DC phenotype modified by DMF is also capable of affecting the T cell response, ovalbumin-specific CD4⁺ T cells were primed with DC under $T_H1$ (CpG/ anti-IL-4 or LPS) or $T_H2$ (IL-4) conditions and compared with DC which had been treated with solvent, DMF or DMF and LPS. After expansion of the $T_H$ cells with IL-2 over 10-12 days, the $T_H$ cells were then restimulated with fresh, irradiated APC and antigen. $IL12^+DC^{GSHhigh}$ which have been treated with solvent or under $T_H1$ conditions induce $T_H1$ cells which produce much IFN-γ and little or no IL-4 (FIG. 2B). On the other hand, IL-4 or DMF treated DC induce $T_H2$ cells which produce much IL-4 and little IFN-γ (FIG. 2C). Even under $T_H1$ conditions (DMF and LPS), $GSH^{low}IL12^-DC$ induce IL-4 producing $T_H2$ cells (FIG. 2B). In addition, IL23-$DC^{GSHlow}$ after stimulation with LPS induce $IL-17T_H$ cells, whereas $IL23^+DC^{GSHhigh}$ induce $IL-17^+ T_H$ cells.

Figure 3A:
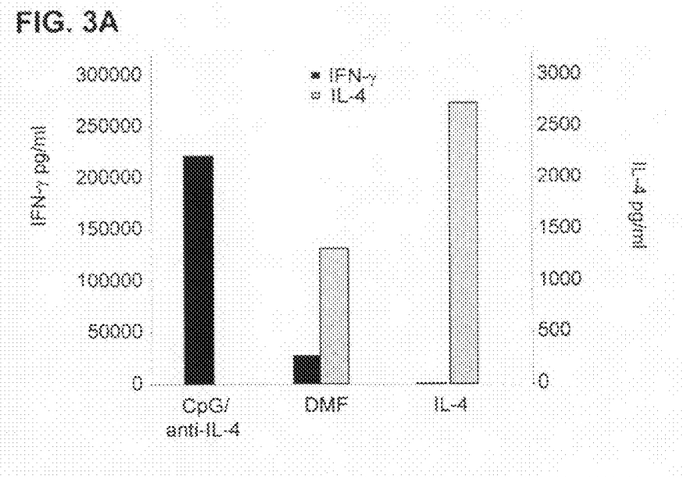
FIG. 3A/B. Determination of IFN-γ and IL-4 using ELISA: similarly to IL-4, in vitro stimulation of PLP-specific T cells after GSH deprivation of the DC promotes differentiation towards Th2 and inhibits the differentiation of $T_H1$ and $T_H$-17.
Figure 3B:
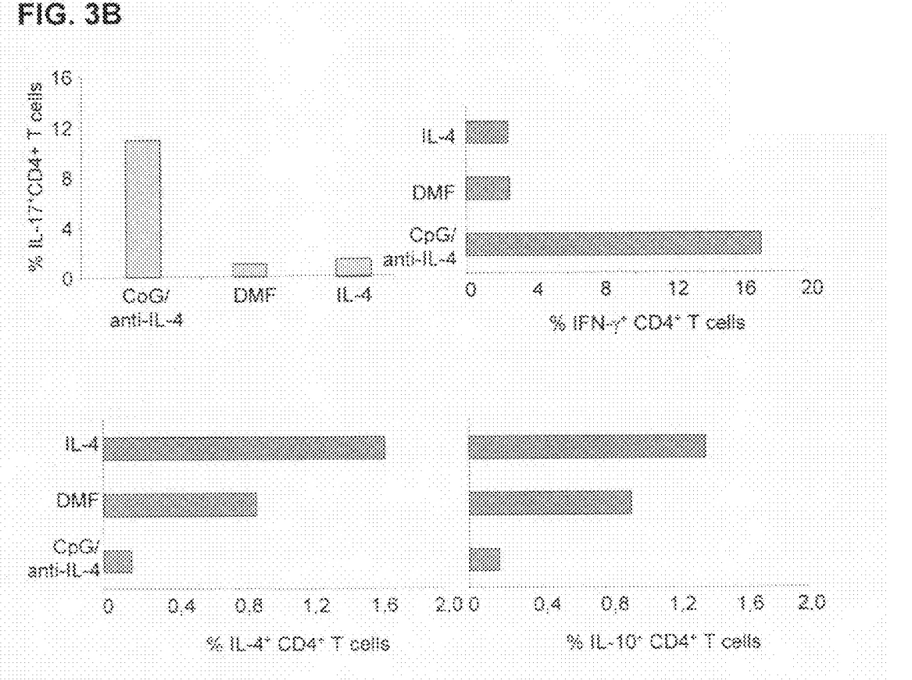

In another system, in which T cells which are directed against a brain-specific protein (proteolipid protein, PLP) were used, similarly to IL-4 the in vitro stimulation of these PLP-specific T cells under GSH-deprivation with DMF promotes the differentiation towards Th2 and inhibits the differentiation of Th1 and Th-17 (FIGS. 3A and B).

Figure 3C:
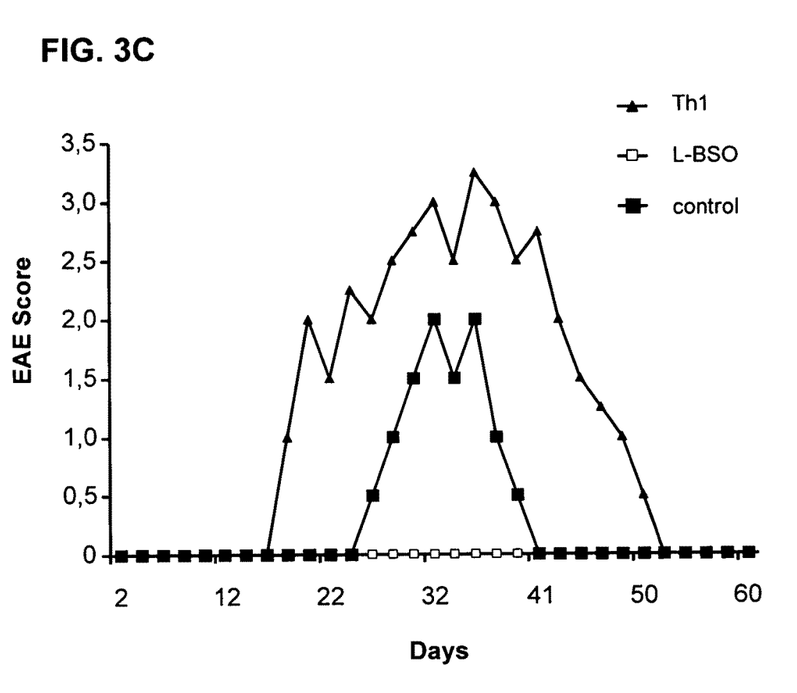
FIG. 3C. Course of EAE with and without treatment: similarly to $T_H2$ cells generated in vitro, in the absence of IL-4, autoreactive T cells generated in vitro under GSH deprivation are almost non-encephalitogenic.

Since the induction of the $T_H2$ phenotype could adversely affect the ability of the $CD4^+$ T cells to induce autoimmune diseases in immunocompetent mice, it was concluded that $GSH^{low}IL12^-DC2$ could weaken the ability of autoreactive $CD4^+$ T cells to induce the disease. For the next experiments, lymphocytes from SJL mice were stimulated twice with PLP peptide, either in the presence or absence of L-BSO, DMF or MMF. After the second stimulation $10^7$ lymphocytes were injected into naive SJL mice. The results of these studies are shown in FIG. 3C by way of example for L-BSO. Autoreactive T cells which were generated with L-BSO in vitro, i.e., under $GSH^{low}$ conditions, were scarcely still capable of inducing EAE in vivo. On the other hand, in vitro differentiated Th1 cells or Th cells which had been activated only with PLP peptide and APC without other stimulants triggered severe encephalomyelitis. PLP-specific T lymphocytes generated in the presence of DMF or MMF were also not able to trigger severe encephalomyelitis (not shown).

Figure 4A:
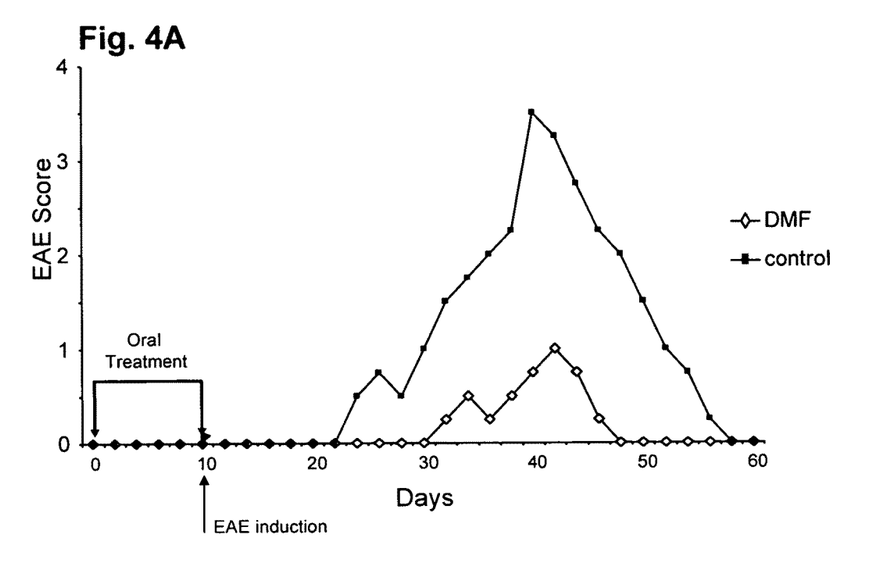
FIG. 4A. Course of EAE with and without treatment: In vivo depletion of GSH by DMF (above) or L-BSO (below) protects actively immunized mice against the onset of severe encephalomyelitis.
Figure 4B:
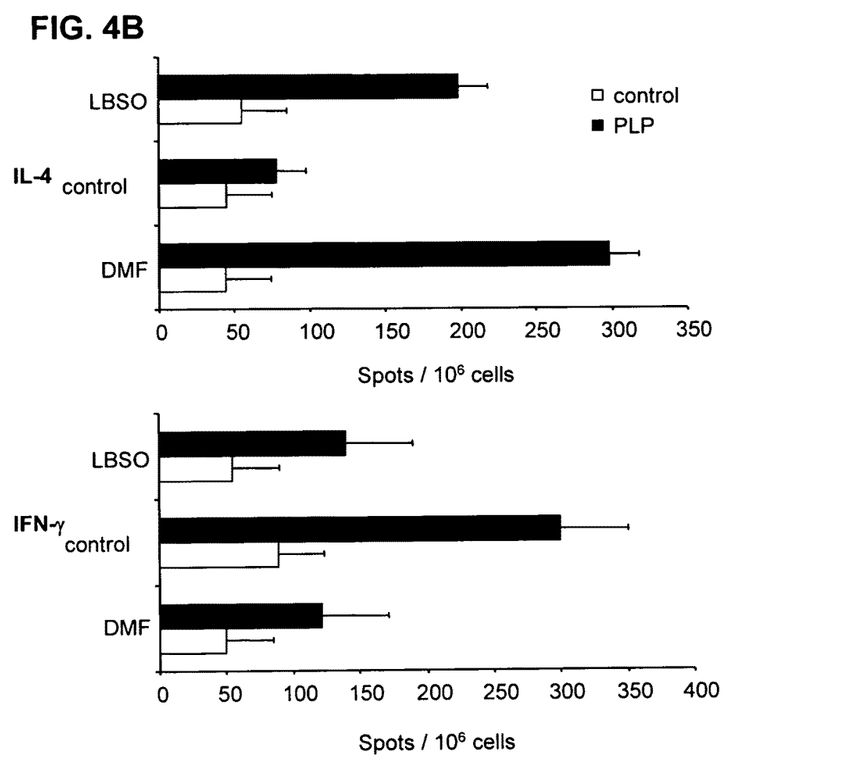
FIG. 4B. Determination of IL-4 and IFN-γ: In vivo depletion of GSH promotes the differentiation of autoreactive $T_H2$ cells.

In order further to study whether GSH deprivation can also influence the differentiation and pathogenicity of autoreactive T cells in vivo, mice were fed with DMF or L-BSO in the drinking water, and the control group only with drinking water. Active EAE induction was effected on day 10 with PLP peptide in complete Freund's adjuvant (CFA) and pertussis toxin. The mice were examined daily regarding the course of the artificially triggered disease. Through the administration of L-BSO or DMF, the GSH levels in lymphoid organs and in the brain of immunized mice could be lowered (not shown). PBS-fed mice developed severe EAE, while L-BSO or DMF-fed mice exhibited markedly milder EAE, some mice even remained healthy (FIGS. 4A+B) and all mice survived. 6 days after immunization, the draining lymph nodes of the mice were analyzed. For this, the $CD4^+$ T cells were isolated and the cytokine production of PLP-specific T cells measured using ELISPOT after in vitro stimulation. $CD4^+$ T cells from DMF and L-BSO fed mice exhibited a $T_H2$-like pattern, whereas PLP-specific $CD4^+$ cells from PBS-treated mice were identified as $T_H1$ cells (FIG. 4B).

Figure 5A:
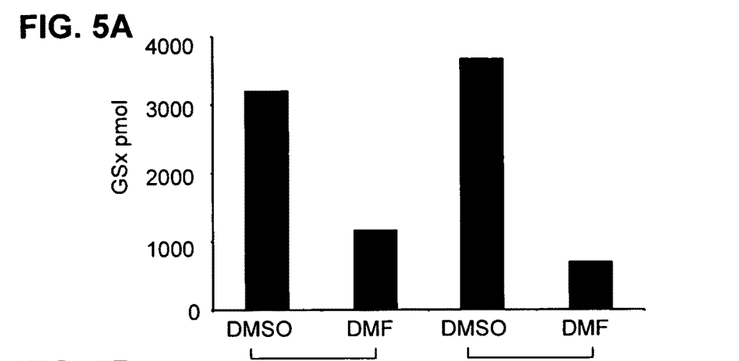
FIG. 5A. Determination of GSH: In vitro depletion of GSH in human DC by DMF.

DMF also depletes GSH in human DC in vitro (FIG. 5A). In order to determine whether GSH deprivation also influences T cell cytokine production in man in vivo, the interferon-γ and interleukin-4 production by $CD4^+$ or $CD8^+$ T cells was determined in 18 patients who were receiving Fumaderm® for treating psoriasis.

Figure 5B:
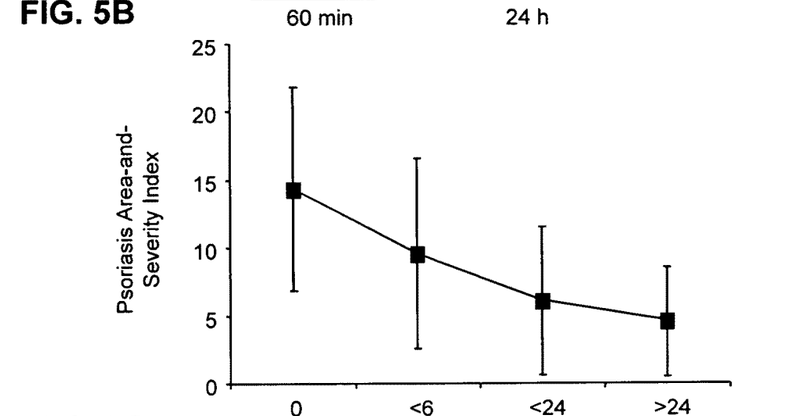
FIG. 5B. Course of PASI in 9 patients treated with Fumaderm®.
Figure 5C:
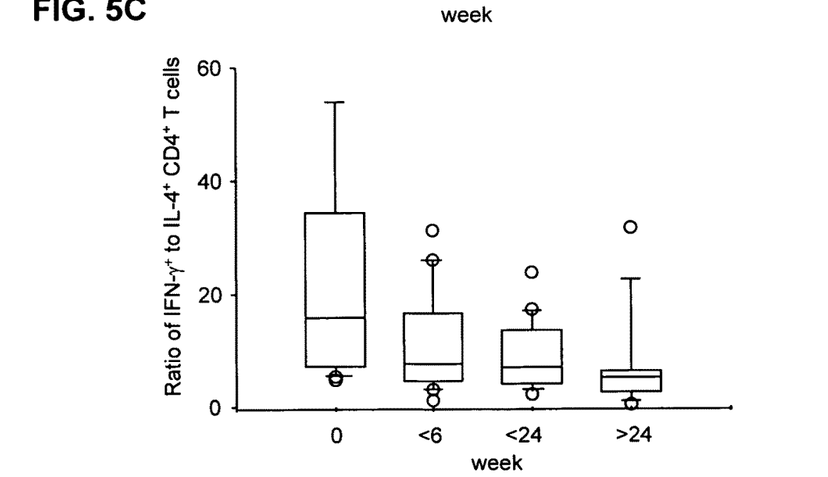
FIG. 5C. Results of the cytokine analyses of peripheral lymphocytes from blood from patients in whom $T_H2$ responses were induced by a GSH-lowering therapy.

Through the experiments, it could be shown that a sustained clinical improvement in the disease was strongly associated firstly with a rise in IL-4 production and then with a lowering of the IFN-γ production of $CD4^+$ cells, which resulted in a constantly suppressed IFN-γ/IL-4 ratio in the $CD4^+$ T cell population (FIG. 5B: Psoriasis Area and Severity Index (PASI) and FIG. 5C: Ratio of the interferon-γ/IL-4+-$CD4+$ T cells in PBMC during Fumaderm® therapy).

Through the experiments performed by the inventors, it could thus be shown that intracellular GSH levels could be modulated by three entirely different approaches: firstly the GSH reservoirs were emptied by the use of thiol-depleting agents; further, GSH synthesis was inhibited with L-BSO and in addition the intracellular GSH level was selectively restored with GSH-OEt. Overall, through these three approaches it could be shown that by means of the intracellular GSH level the DC differentiation could be steered either to $GSH^{high}IL-12^+$ DC1 or $GSH^{low}IL-12^-$ DC2. This regulation is—at least to some extent—an essential step in IL-12 production. The differences in IL-12 production also explain the ability of $GSH^{high}$ DC1 or $GSH^{low}DC2$ to induce $T_H1$ or $T_H2$ respectively.

Hence with the present invention, i.e., the deliberate lowering of the cellular GSH level by certain substances, a new approach is presented for the therapy of autoimmune diseases, and for diseases in general which can be treated by lowering of the GSH levels.

Example II

For the testing of the potential of pharmaceutical substances to lower the glutathione content of cells, the following procedure was carried out: cells (antigen-presenting cells or dendritic cells) are incubated with different concentrations of the given pharmaceutical substance to be tested. Then, after an incubation time of 1 hr, 2 hrs, 24 hrs or 48 hrs, the glutathione content of the cells is determined in comparison to control cells. For this, after the incubation time, the cells are lysed with 1% sulfosalicylic acid (SSA) and incubated on ice. The lysate is then high-speed centrifuged and the supernatant used for the GSH measurement, and the sediment prepared for the protein measurement after Lowry.

The samples and the GSH standard were diluted in a microtiter plate and the assay reaction started by addition of a reaction mix which contains glutathione reductase. The composition of the reaction mix was as follows: 92.7 µl GSH buffer (0.1 M sodium phosphate, $Na_2HPO_4$ and $NaH_2PO_4$ $2H_2O$, Roth, Karlsruhe, Germany), 4 µl 10 mM NADPH (tetrasodium salt, AppliChem, Darmstadt, Germany), 3 µl 10 mM DTNB (5,5'-dithiobis(2-nitro-benzoic acid), Sigma) and 0.64 µl glutathione reductase (GR, Roche Applied Science, Grenzach-Wyhlen, Germany). The rise in the extinction is measured at 405 nm at 30 sec intervals over 10 mins with a microtiter plate reader. The glutathione content was determined using a calibration curve. In order to measure the glutathione disulfide (GSSG) content of the cells, i.e., the oxidized form of glutathione, the GSH, i.e., the reduced form, in the sample had to be masked with 2-vinyl-pyridine at a pH between 5 and 7. For the measurement of the protein content of each sample, the cell pellet after lysis was dried and taken up in 0.5 M NaOH. The protein content was determined by the method of Lowry (see for example, Dringen, et al., "Supply by Astrocytes of CysGly as Precursor for neuronal Glutathione", *J. Neurosci* 19:562-569). Bovine serum albumin was used as the standard.

The pharmaceutical substances to be tested can also be analyzed ex vivo for their potential to deplete GSH. For this, after treatment of experimental mice, small tissue pieces are removed from the respective organs and placed in about 1 ml of 1% SSA. The tissue piece in SSA is homogenized using an ultrasonic probe. The further GSH and protein determination is effected according to the procedure described for APC and DC. Comparison with the GSH content of control cells or control tissue indicates the GSH-lowering action of the pharmaceutical substance to be tested.

Example III

For testing the potential of pharmaceutical substances to induce the ROS, the following procedure was developed: for the measurement of reactive oxygen species (ROS) in cells, the fluorescent dye 2',7' dichlorofluorescein ($H_2$ DCFDA) is used. The absorption spectrum of the substance is 492-495 nm and the emission spectrum lies in the range between 517-527 nm. On induction of cell stress, e.g., by the administration of ROS-causing reagents, oxidation of the $H_2$ DCFDA to DCFDA+$H_2$ occurs. The fluorescence arising as a result can be detected using flow cytometry (FL1).

The invention claimed is:

1. A method for treating multiple sclerosis in a human in need thereof, which method comprises administering to the human a therapeutically effective amount of a substance which lowers the cellular glutathione content, wherein the substance is L-BSO.

2. The method as claimed in claim 1, wherein the substance is administered with physiologically compatible additives and/or carrier substances.

3. The method as claimed in claim 1, wherein one or more additional substances which lower the cellular glutathione level are administered.

4. The method as claimed in claim 1, wherein a daily dosage of L-BSO of 0.001 mg/kg body weight of a patient to 100 mg/kg body weight of a patient is administered.

5. The method as claimed in claim 1, wherein the substance is orally, parenterally, buccally, nasally, transdermally or intradermally administered.

6. The method as claimed in claim 1, wherein the substance is administered in the form of a capsule, depot capsule, tablet or unit dose of an injection.

* * * * *